United States Patent
Chang et al.

(10) Patent No.: US 9,760,689 B2
(45) Date of Patent: Sep. 12, 2017

(54) COMPUTER-AIDED DIAGNOSIS METHOD AND APPARATUS

(71) Applicant: Samsung Electronics Co., Ltd., Suwon-si (KR)

(72) Inventors: Chu-Ho Chang, Seoul (KR); Yeong-Kyeong Seong, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 88 days.

(21) Appl. No.: 14/026,509

(22) Filed: Sep. 13, 2013

(65) Prior Publication Data

US 2014/0142413 A1 May 22, 2014

(30) Foreign Application Priority Data

Nov. 16, 2012 (KR) .................. 10-2012-0130481

(51) Int. Cl.
G06K 9/00 (2006.01)
G06F 19/00 (2011.01)

(52) U.S. Cl.
CPC .......... *G06F 19/345* (2013.01); *G06F 19/321* (2013.01)

(58) Field of Classification Search
None
See application file for complete search history.

(56) References Cited

U.S. PATENT DOCUMENTS

| | | | |
|---|---|---|---|
| 4,945,476 A | 7/1990 | Bodick et al. | |
| 7,783,094 B2 | 8/2010 | Collins et al. | |
| 8,014,576 B2 | 9/2011 | Collins et al. | |
| 8,391,574 B2 | 3/2013 | Collins et al. | |
| 2005/0020903 A1 | 1/2005 | Krishnan et al. | |
| 2005/0049497 A1* | 3/2005 | Krishnan et al. | 600/437 |
| 2006/0274928 A1 | 12/2006 | Collins et al. | |
| 2009/0082637 A1 | 3/2009 | Galperin | |
| 2010/0250275 A1 | 9/2010 | Sakagawa et al. | |
| 2011/0137132 A1 | 6/2011 | Gustafson | |
| 2012/0020536 A1 | 1/2012 | Moehrle | |
| 2012/0130223 A1* | 5/2012 | Reicher | 600/407 |

FOREIGN PATENT DOCUMENTS

| | | |
|---|---|---|
| CN | 1839391 A | 9/2006 |
| CN | 1914617 A | 2/2007 |
| JP | 2011-212094 | 10/2011 |
| JP | 2012-135428 | 7/2012 |
| KR | 10-2008-0021723 | 3/2008 |
| KR | 10-2010-0065194 | 6/2010 |
| WO | 2011/132097 A2 | 10/2011 |

OTHER PUBLICATIONS

Yulei Jiang, "Computer-Aided Diagnosis of Digital Mammograms", Jun. 2004, pp. 1-13, The University of Chicago, Chicago, Illinois 60637.

(Continued)

*Primary Examiner* — Atiba O Fitzpatrick (74) *Attorney, Agent, or Firm* — Jefferson IP Law, LLP (57) ABSTRACT

A computer-aided diagnosis (CAD) method includes extracting a lesion feature value of a lesion feature of a lesion from a captured lesion image; receiving additional information; and diagnosing the lesion based on a combination of the extracted lesion feature value and the received additional information.

22 Claims, 6 Drawing Sheets

(56) References Cited

OTHER PUBLICATIONS

Yulei Jiang, Robert A. Schmidt, Robert M. Nishikawa, Carl J. D'Orsi*, Carl J. Vyborny, Gillian M. Newstead, "Use of BI-RADS lesion descriptors in computer-aided diagnosis of malignant and benign breast lesions", 2004, pp. 199-202, Department of Radiology, The University of Chicago, Chicago, IL 60637, *Department of Radiology, Emory University, Atlanta, GA 30322.

Bei Liu, Charles E. Metz, and Yulei Jiang, "An ROC comparison of four methods of combining information from multiple images of the same patient", Sep. 2004, pp. 2552-2563, vol. 31 No. 9.

Sophie Paquerault, Laura M. Yarusso, John Papaioannou, Yulei Jiang, and Robert M. Nishikawa, "Radial gradient-based segmentation of mammographic microcalcifications: Observer evaluation and affect on CAD performance", Sep. 2004, pp. 2648-2657, Department of Radiology, The University of Chicago, 5841 South Maryland Avenue, MC 2026, Chicago, Illinois 60637.

Yulei Jiang, Rich S. Rana, Robert A. Schmidt, Robert M. Nishikawa, Bei Liu, Charlene A. Sennett, James J. Chambliss, Hiroyuki Abe, "Computer Classification of Malignant and Benign Calcifications in Full-Field Digital Mammograms", Department of Radiology, The University of Chicago.

Robert M. Nishikawa, Yulei, Ingrid Reiser, "What is the Required Pixel Size for Digital Mammography?", pp. 1-9, Department of Radiology, the University of Chicago.

R. M. Zur*, Y. Jiang, C.E. Metz, "Comparison of two methods of adding jitter to artificial neural network training", 2004, pp. 886-889, Department of Radiology MC2026, the University of Chicago, 5841 South Maryland Avenue, 30637, Chicago, IL USA.

* cited by examiner

COMPUTER-AIDED DIAGNOSIS METHOD AND APPARATUS

CROSS-REFERENCE TO RELATED APPLICATIONS

This application claims the benefit under 35 USC 119(a) of Korean Patent Application No. 10-2012-0130481 filed on Nov. 16, 2012, in the Korean Intellectual Property Office, the entire disclosure of which is incorporated herein by reference for all purposes.

BACKGROUND

1. Field

The following description relates to a method and apparatus for computer-aided diagnosis (CAD).

2. Description of Related Art

CAD is a technique to detect a lesion from a captured image, diagnose the detected lesion and present a diagnosis result to a user to help the user diagnose the lesion. A precise CAD diagnosis helps the user establish a final diagnosis. The precision of diagnosis through CAD may be lowered because captured lesion images such as sonograms may suffer from various problems such as low resolution, low contrast, speckle noise, and blurred lesion boundaries.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a computer-aided diagnosis (CAD) method includes extracting a lesion feature value of a lesion feature of a lesion from a captured lesion image; receiving additional information; and diagnosing the lesion based on a combination of the extracted lesion feature value and the received additional information.

The diagnosing may include comparing the extracted lesion feature value and the received additional information with a lesion diagnosis model; and diagnosing the lesion based on a result of the comparing.

The lesion diagnosis model may be generated based on a plurality of lesion feature values extracted from previously captured lesion images; and a plurality of additional information for the previously captured lesion images.

The lesion diagnosis model may includes combinations of the plurality of lesion feature values extracted from the previously captured lesion images and the plurality of additional information; and diagnosis results corresponding to the combinations.

The additional information may include any one or any combination of information about the lesion determined by a user based on the captured lesion image; and medical records and patient information that affect a diagnosis of the lesion.

The receiving may include receiving the additional information from a user through a user interface; and the user interface may include a lesion image display area configured to display the captured lesion image; and an additional information input area configured to receive the additional information from the user.

The additional information input area may be further configured to display one or more additional information fields for selection by the user; and in response to one of the additional information fields being selected by the user, display one or more sub-fields of the selected additional information field.

The additional information input area may be further configured to display one or more additional information fields for the lesion feature in response to the extracted lesion feature value being less than a reference value.

The additional information input area may be further configured to display one or more additional information fields having a greater influence on a diagnosis of the lesion differently from one or more additional information fields having a lesser influence on the diagnosis of the lesion.

The additional information input area may be further configured to receive text-type additional information from the user.

The additional information input area may be further configured to receive audio-type additional information from the user.

In another general aspect, a computer-aided (CAD) apparatus includes a lesion feature extractor configured to extract a lesion feature value of a lesion feature of a lesion from a captured lesion image; an interface configured to receive additional information; and a diagnoser configured to diagnose the lesion based on a combination of the extracted lesion feature value and the received additional information.

The CAD apparatus may further include a database configured to store a lesion diagnosis model; and the diagnoser may be further configured to compare the extracted lesion feature value and the received additional information with the lesion diagnosis model; and diagnose the lesion based on a result of the comparing.

The lesion diagnosis model may be generated based on a plurality of lesion feature values extracted from previously captured lesion images; and a plurality of additional information for the previously captured lesion images.

The lesion diagnosis model may include combinations of the plurality of lesion feature values extracted from the previously captured lesion images and the plurality of additional information; and diagnosis results corresponding to the combinations.

The additional information may include any one or any combination of results of information about the lesion determined by a user based on the captured lesion image; and medical records and patient information that affect a diagnosis of the lesion.

The interface may include a user interface configured to receive the additional information from a user; and the user interface may include a lesion image display area configured to display the captured lesion image; and an additional information input area configured to receive the additional information from the user.

The additional information input area may be further configured to display one or more additional information fields for selection by a user; and in response to one of the additional information fields being selected by the user, display one or more sub-fields of the selected additional information field.

The user interface may be further configured to display one or more additional information fields for the lesion feature in response to the extracted lesion feature value being less than a reference value.

The user interface may be further configured to display one or more additional information fields having a greater influence on a diagnosis of the lesion differently from one or more additional information fields having a lesser influence on the diagnosis of the lesion.

The additional information input area may be further configured to receive text-type additional information from the user.

In another general aspect, a method of generating a lesion diagnosis model includes extracting at least one lesion feature value from each of a plurality of captured lesion images; receiving additional information for each of the captured lesion images; generating combinations of the lesion feature values and the additional information; and generating a lesion diagnosis model based on the combinations of the lesion feature values and the additional information, and diagnosis results corresponding to the combinations.

Each of the combinations may include at least one lesion feature value and at least one item of additional information; and each of the diagnosis results may correspond to at least one of the combinations.

The additional information may include information about lesion features from which the lesion feature values were extracted.

The additional information further may include medical records and patient information affecting a diagnosis of a lesion from which the lesion feature values were extracted.

The receiving may include receiving the additional information from a user; and the diagnosis results corresponding to the combinations may be determined by the user based on the captured lesion images.

Other features and aspects will be apparent from the following detailed description, the drawings, and the claims.

DETAILED DESCRIPTION

The following description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

Figure 1:
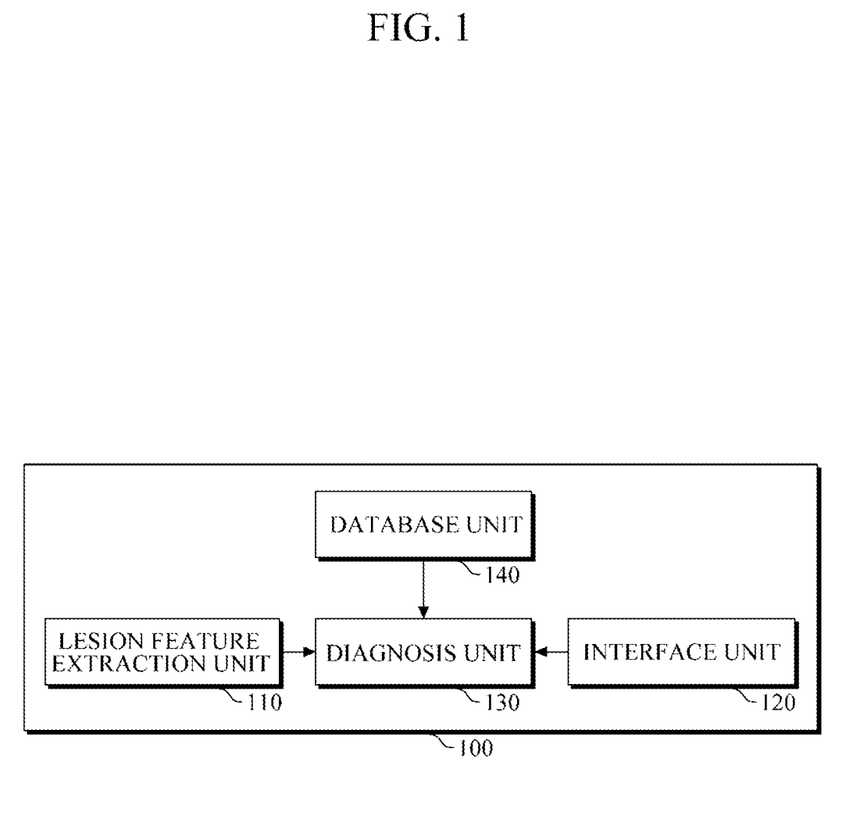
FIG. 1 is a diagram illustrating an example of a computer-aided diagnosis (CAD) apparatus.

FIG. 1 is a diagram illustrating an example of a computer-aided diagnosis (CAD) apparatus. Referring to FIG. 1, a CAD apparatus 100 includes a lesion feature extraction unit 110, an interface unit 120, a diagnosis unit 130, and a database unit 140.

The lesion feature extraction unit 110 extracts a lesion feature value from a captured lesion image input to the CAD apparatus 100. As non-exhaustive examples only, the captured lesion image may be a computed radiography (CR) image, a computed tomography (CT) image, a sonogram, a magnetic resonance imaging (MRI) image. The lesion feature value is a value representing one of the features of a lesion that is associated with determining the malignancy of the lesion. The lesion feature value may be extracted from the captured lesion image through image processing. As a non-exhaustive example only, the lesion feature value may be a computer-recognizable value obtained by analyzing a lesion in the captured lesion image, and may represent the structural characteristics and texture of the lesion.

The lesion feature extraction unit 110 may analyze a lesion in the captured lesion image to obtain the lesion feature value. For example, the lesion feature extraction unit 110 may search for a lesion, segment a lesion found in the search, and extract a lesion feature value from the segmented lesion. In another example, the lesion feature extraction unit 110 may receive an input from a user selecting a lesion in the captured lesion image and the lesion feature extraction unit 110 may extract a lesion feature value from the lesion selected by the user. Various methods for searching for a lesion, segmenting a lesion, and extracting a feature value from a lesion are well known to one of ordinary skill in the art, and thus will not be described in detail here.

The interface unit 120 receives additional information from the user. The additional information entered by the user may include a variety of information that may affect the diagnosis of the lesion. The additional information may include lesion information determined by the user from the captured lesion image, such as, for example, the structural characteristics of a lesion (for example, shape, margin, and boundary), or the texture of a lesion. For example, in response to the captured lesion image being a breast image, the additional information may include the characteristics of a lesion that are determined by the user through the analysis of the captured lesion image according to the Breast Imaging Reporting and Data System (BI-RADS) lexicon classification. In another example, the additional information may include medical records and information concerning a patient, such as, for example age, sex, occupation, sexual activity, smoking habits, drinking habits, drug use, current illnesses, chronic diseases, medication use, blood-sugar levels, blood pressure, and pregnancy. The lesion feature value may be automatically extracted from the captured lesion image by the lesion feature extraction unit 110, whereas the additional information includes information determined by the user based on the captured lesion image.

The interface unit 120 may include a display and an input. The display may include one or more screens used to display information to a user. As non-exhaustive examples only, the display may be implemented as a liquid crystal display (LCD), a light-emitting diode (LED) display, a plasma display panel (PDP), a screen, or a terminal. Likewise, the input may include any structure that includes one or more hardware components to enable receipt of a user's input. The interface unit 120 may display a user interface on the display to receive the additional information from the user, and thus the display may also serve as the input. As non-exhaustive examples only, the input may be implemented as any one or any combination of a mouse, a keyboard, a soft keyboard, a screen, a microphone, a click wheel, a display, and a terminal.

A screen may be a physical structure that includes one or more hardware components that provide the ability to render a user interface and/or receive user input. The screen can encompass any combination of a display region, a gesture capture region, a touch sensitive display, and/or a configurable area. The screen can be embedded in the hardware, or may be an external peripheral device that may be attached and detached from the apparatus. The display or input may be a single-screen or a multi-screen display or input. A single physical screen can include multiple displays that are managed as separate logical displays permitting different content to be displayed on separate displays although part of the same physical screen.

A terminal (which is sometimes referred to as a computer terminal) may be an electronic or electromechanical hardware device that is used for entering data into, and displaying data from, a host computer or a host computing system. The function of a terminal can be confined to display and input of data. A terminal with significant local programmable data processing capability may be called a "smart terminal" or a fat client. A terminal that depends on the host computer for its processing power is called a thin client. A personal computer can run software that emulates the function of a terminal, sometimes allowing concurrent use of local programs and access to a distant terminal host system.

The diagnosis unit 130 determines whether the lesion is benign or malignant based on the lesion feature value extracted from the captured lesion image and the additional information provided by the user. The diagnosis unit 130 may determine whether the lesion is benign or malignant by comparing the lesion feature value extracted by the lesion feature extraction unit 110 and the additional information entered by the user with a lesion diagnosis model stored in database unit 140.

The lesion diagnosis model may be generated by performing learning based on lesion feature values extracted from a plurality of captured lesion images captured in advance and additional information provided for each of the lesion images. The lesion diagnosis model results diagnosis results corresponding to the various permutations and combinations of the lesion feature values and the additional information. That is, the lesion diagnosis model may include combinations of lesion feature values and additional information, and diagnosis results respectively corresponding to the combinations. Each combination may include at least one lesion feature value and at least one additional information, and the diagnosis results may include a diagnosis result corresponding to each combination. A particular diagnosis result may correspond to several different combinations. That is, several different combinations may have the same diagnosis result. A user may determine a diagnosis result for each combination based on the captured lesion images as part of the process of generating the lesion diagnosis model.

The diagnosis unit 130 may perform a lesion diagnosis by comparing the lesion feature value extracted by the lesion feature extraction unit 110 and the additional information entered by the user with the lesion feature value-additional information combinations of the lesion diagnosis model stored in database unit 140. The diagnosis unit 130 may perform the lesion diagnosis by searching for a lesion feature value-additional information combination of the lesion diagnosis model stored in the database unit 140 that most closely matches the lesion feature value extracted by the lesion feature extraction unit 110 and the additional information entered by the user, and retrieving the diagnosis result corresponding to the closest lesion feature value-additional information combination from the lesion diagnosis model as the lesion diagnosis for the lesion feature value extracted by the lesion feature extraction unit 110 and the additional information entered by the user.

In the example illustrated in FIG. 1, the characteristics of a lesion that are extracted from the captured lesion image by the user and various information to be considered in connection with the determination of the malignancy or benignancy of the lesion may be used as additional information together with the lesion feature value extracted by the lesion feature extraction unit 110. Accordingly, the precision of the diagnosis of the lesion may be improved even when the lesion feature value extracted by the lesion feature extraction unit 110 is not very precise.

Figure 2:
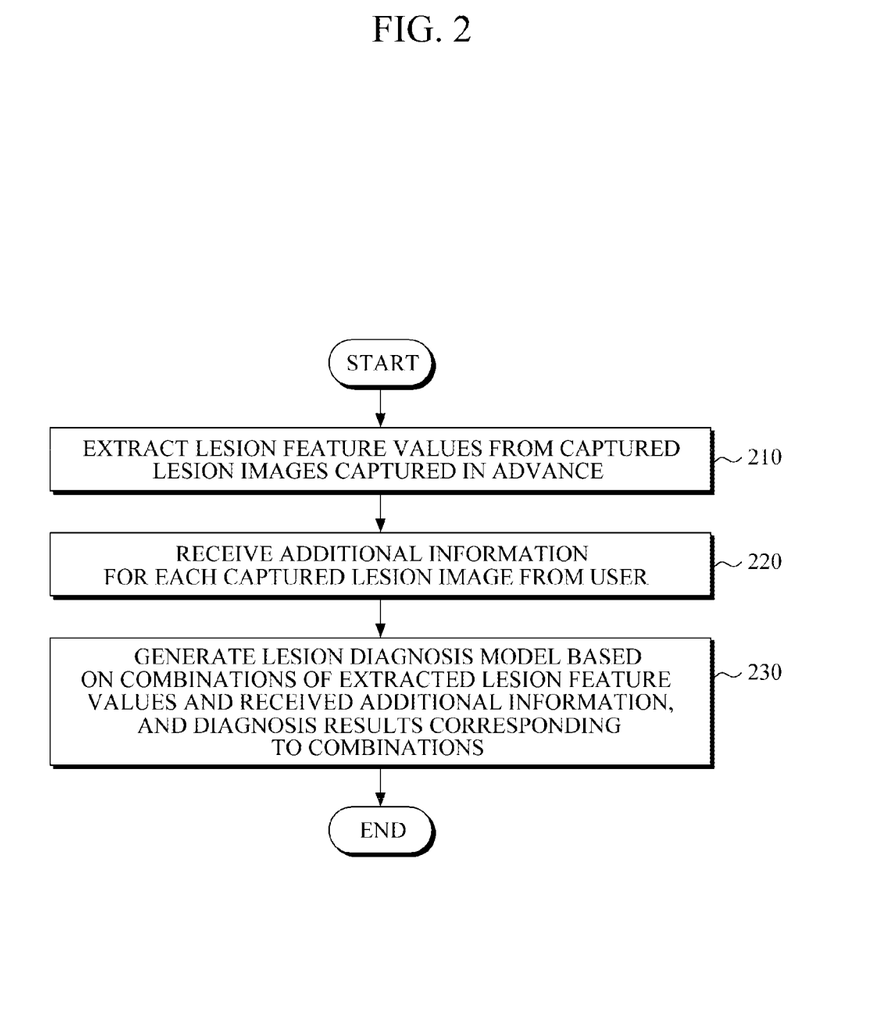
FIG. 2 is a diagram illustrating an example of generating a lesion diagnosis model.

FIG. 2 is a diagram illustrating an example of generating a lesion diagnosis model. The operations in FIG. 2 may be performed in the sequence and manner as shown, although the order of some operations may be changed without departing from the spirit and scope of the illustrative examples described. Many of the operations shown in FIG. 2 may be performed in parallel or concurrently. The description of FIG. 1 is also applicable to FIG. 2, and thus will not be repeated here.

Referring to FIG. 2, lesion feature values are extracted (210) from captured lesion images that are captured in advance. Additional information for each of the captured lesion images is received from a user (220).

A lesion diagnosis model is generated (230) by performing learning based on the combinations of the lesion feature values extracted in operation 210 and the additional information entered by the user in operation 220, and diagnosis results corresponding to the lesion feature value-additional information combinations. The user may determine a diagnosis result for each lesion feature value-additional information combination based on the captured lesion image from which the lesion feature value was extracted. Various machine learning algorithms that are well known to one of ordinary skill in the art, such as, for example, a support vector machine (SVM), may be used to generate the lesion diagnosis model, and will not be described in detail here. The lesion diagnosis model may be generated and stored in advance in the database unit 140.

Figure 3A:
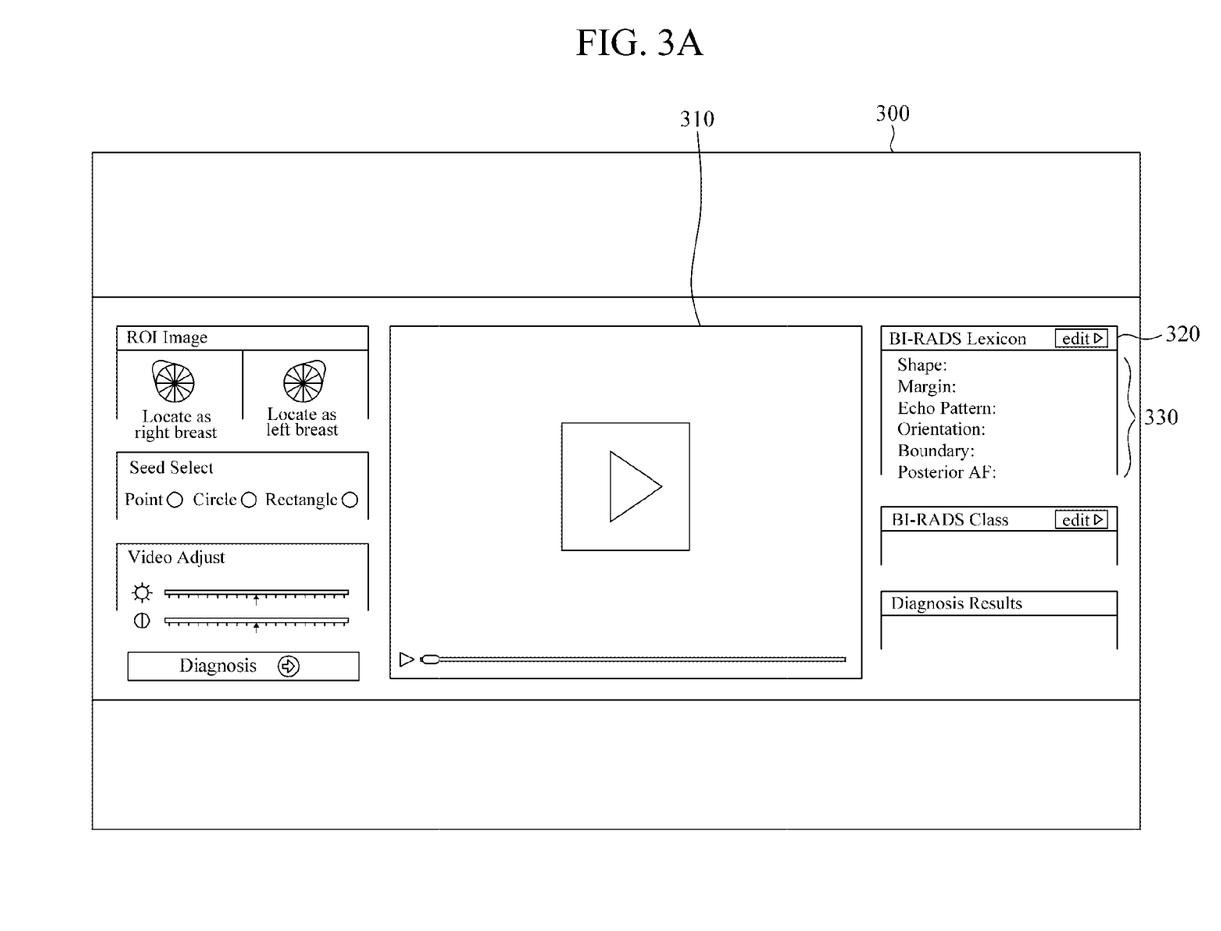
FIGS. 3A to 3C are diagrams illustrating examples of various states of an example of a user interface for entering additional information.
Figure 3B:
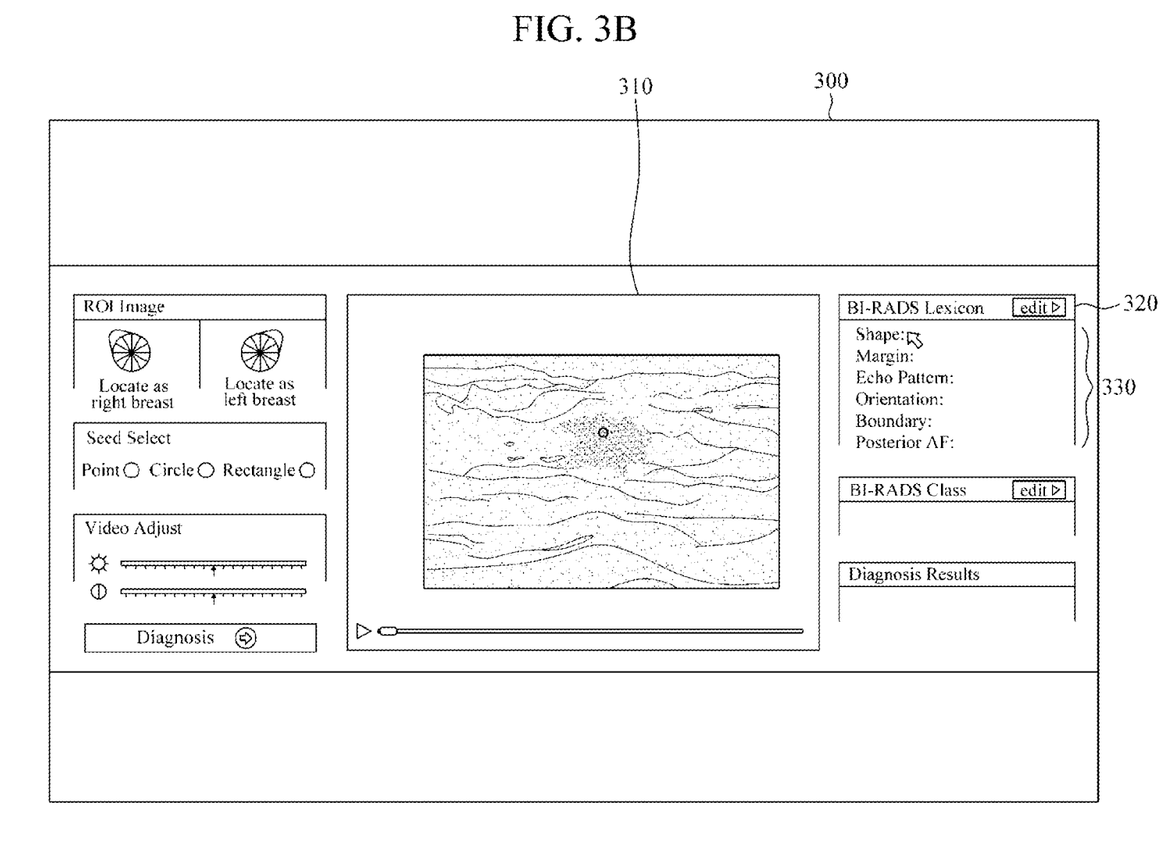
Figure 3C:
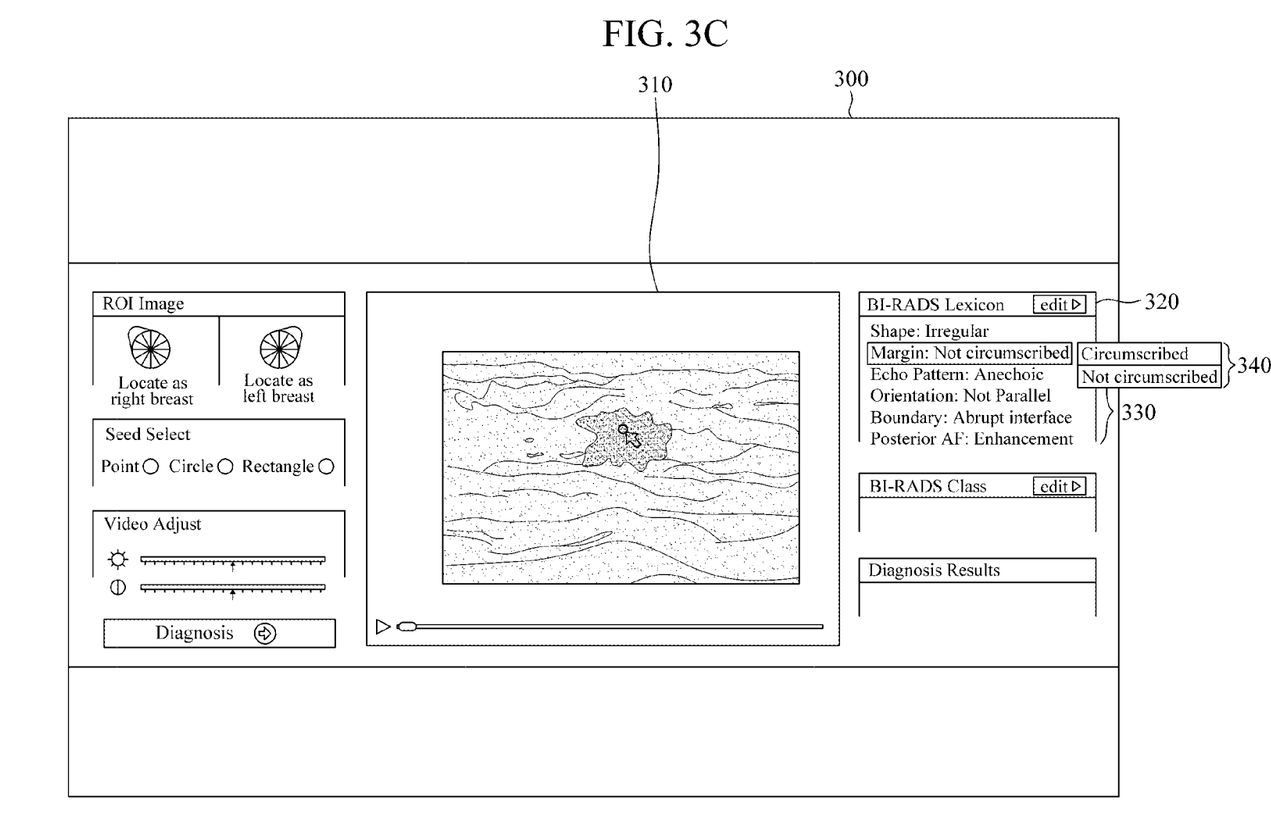

FIGS. 3A to 3C are diagrams illustrating examples of various states of an example of a user interface for entering additional information. In the example illustrated in FIGS. 3A to 3C, additional information in accordance with the BI-RADS lexicon classification may be entered via a user interface 300. Referring to FIG. 3A, the user interface 300 may include a lesion image display area 310 in which to display a captured lesion image, and an additional information input area 320 in which to enter additional information. The lesion image display area 310 may display a captured lesion image input into the CAD apparatus 100.

The additional information input area 320 enables a user to enter additional information, and may display a list of one or more additional information fields 330. The additional information fields 330 may enable the user to choose one of the additional fields and enter additional information in the chosen additional information field 330.

Additional information fields 330 that have a greater effect on the diagnosis of a lesion may be displayed differently, such as, for example, in a different color, size, orientation, shape, or highlighted, from additional information fields 330 having a lesser effect on the diagnosis of the lesion. The additional information fields 330 having a greater effect on the diagnosis of a lesion may be associated with additional information that may considerably affect the diagnosis of a lesion based on a result of comparing a lesion feature value extracted by the lesion feature extraction unit 110 with a lesion diagnosis model.

Referring to FIG. 3B, the user may choose one of the additional information fields 330 in which to enter additional information. In the example illustrated in FIG. 3B, the user has chosen the additional information field 330 "Shape" as indicated by the arrow. In response to the user choosing one of the additional information fields 330, a number of sub-fields 340 of the chosen additional information field 330 may be displayed as shown in FIG. 3C.

Referring to FIG. 3C, in response to the user choosing one of the additional information fields 330, sub-fields 340 of the additional information field 330 may be displayed, and the user may select one of the sub-fields 340. For example, when a BI-RADS lexicon classification value is to be entered as additional information in FIG. 3C, Bi-RADS lexicon categories, such as "Shape," "Margin," "Echo Pattern," "Orientation," "Boundary," and "Posterior," may be displayed as the additional information fields 330. In response to the user selecting, for example, the "Margin" field, "Circumscribed" and "Not Circumscribed" may be displayed as sub-fields 340 of the "Margin" field. Although not illustrated in FIG. 3C, other sub-fields of the "Margin" field, for example, "Spiculated," "Angular," and "Microlobulated," may also be displayed.

In this example, the likelihood that each of the sub-fields of the "Margin" field is a correct representation of a given lesion may be calculated by comparing a lesion feature value associated with the margin of the given lesion and extracted by the lesion feature extraction unit 110 with a lesion diagnosis model, and the sub-fields of the "Margin" field may be displayed in order of their relevance to the given lesion based on the results of the calculation, that is, in order of the likelihood that are a correct representation of the given lesion.

If a lesion feature value extracted by the lesion feature extraction unit 110 is less than a predetermined reference value, additional information input area 320 may display a list of one or more additional information fields 330 for the corresponding lesion feature. For example, the extracted lesion feature value may not be precise enough to properly determine the shape of a lesion due to a low resolution of the captured lesion image from which the lesion feature value was extracted, or noise in the captured lesion image. In this case, a list of one or more additional information fields regarding the shape of a lesion may be presented to the user to enable the user to enter additional information regarding the shape of the lesion. The predetermined reference value may be set in advance by the user.

A method of entering additional information is not limited to the example illustrated in FIGS. 3A to 3C. In another example, the additional information input area 320 may be configured to enable the user to enter text-type additional information. In yet another example, the additional information input area 320 may be configured to enable the user to enter audio-type additional information with the use of an input device such as, for example, a microphone. In yet another example, the additional information input area 320 may be configured to enable the user to choose an additional information field 330 and enter text-type additional information into the chosen additional information field 330.

Figure 4:
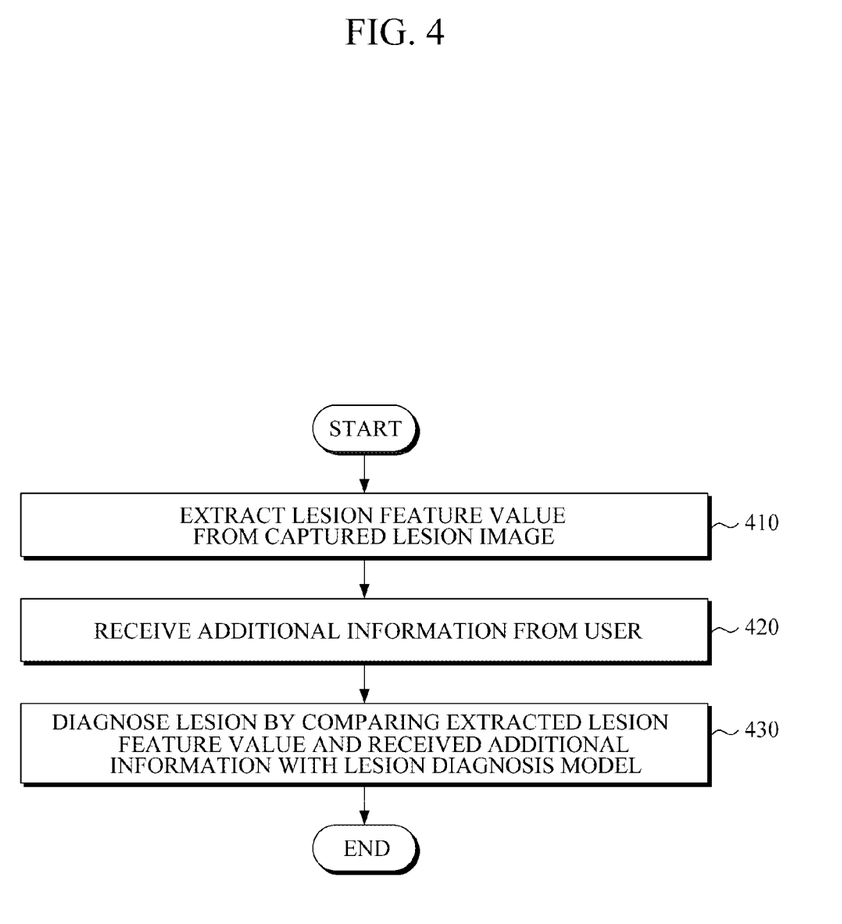
FIG. 4 is a diagram illustrating an example of a CAD method.

FIG. 4 is a diagram illustrating an example of a CAD method. The operations in FIG. 4 may be performed in the sequence and manner as shown, although the order of some operations and the like may be changed without departing from the spirit and scope of the illustrative examples described. Many of the operations shown in FIG. 4 may be performed in parallel or concurrently. The description of FIG. 1 is also applicable to FIG. 4, and thus will not be repeated here.

Referring to FIG. 4, the CAD apparatus 100 extracts a lesion feature value from a captured lesion image input to the CAD apparatus (410). The CAD apparatus 100 receives additional information from a user (420). The additional information may be entered via a user interface as described above with reference to FIGS. 1 and 3A to 3C.

The CAD apparatus 100 diagnoses a lesion (430) by comparing the lesion feature value extracted in operation 410 and the additional information received in operation 420 with a lesion diagnosis model stored in the CAD apparatus 100 in advance, and diagnosing the lesion based on a result of the comparing. The diagnosis result may indicate whether the lesion is benign or malignant, or the degree of benignancy/malignancy of the lesion.

The CAD apparatus 100 may search for and find in the lesion diagnosis model a lesion feature value-additional information combination that most closely matches the lesion feature value extracted in operation 410 and the additional information received in operation 420, and may retrieve a diagnosis result for the found lesion feature value-additional information combination from the lesion diagnosis model as a diagnosis result for the lesion feature value extracted in operation 410 and the additional information received in operation 420.

That is, by using both a lesion feature value automatically extracted from a captured lesion image and additional information entered manually by the user, the precision of a diagnosis of a lesion based on a captured lesion image may be improved even when the captured lesion image suffers from various problems such as low resolution, low contrast, speckle noise, and blurred lesion boundaries.

The CAD apparatus 100, the lesion feature extraction unit 110, the interface unit 120, the diagnosis unit 130, and the database unit 140 illustrated in FIG. 1 and the user interface 300 illustrated in FIGS. 3A-3C that perform the operations illustrated in FIGS. 2 and 4 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A computer-aided diagnosis (CAD) method performed at a processor, the method comprising:
    extracting at least one lesion feature value from a captured lesion image comprising at least one lesion;
    receiving, at a user interface, at least one additional information comprising information needed to diagnose the at least one lesion based on the captured lesion image,
    wherein the user interface comprises:
        a lesion image display area configured to display the captured lesion image, and
        an additional information input area configured to:
            receive the at least one additional information,
            display at least one additional information field for selection by a user, and
            in response to one of the at least one additional information field being selected by the user, display at least one sub-field of the selected additional information field;
    diagnosing the at least one lesion based on the extracted at least one lesion feature value and the received at least one additional information; and
    displaying the captured lesion image,
    wherein the at least one additional information, that is based on the captured lesion image, affects a diagnosis of the at least one lesion.

2. The CAD method of claim 1, wherein the diagnosing comprises:
    comparing the extracted at least one lesion feature value and the received at least one additional information with a lesion diagnosis model; and diagnosing the at least one lesion based on a result of the comparing.

3. The CAD method of claim 2, wherein the lesion diagnosis model is generated based on:
   at least one lesion feature value extracted from previously captured lesion images; and
   at least one additional information for the previously captured lesion images.

4. The CAD method of claim 3, wherein the lesion diagnosis model comprises:
   at least one combination of the at least one lesion feature value extracted from the previously captured lesion images and the at least one additional information for the previously captured lesion images; and
   at least one diagnosis result corresponding to the at least one combination.

5. The CAD method of claim 1, wherein the at least one additional information comprises at least one medical record and patient information that affect the diagnosis of the at least one lesion.

6. The CAD method of claim 1, wherein the additional information input area is further configured to display, if at least one of the extracted at least one lesion feature value is less than a reference value, at least one additional information field for at least one corresponding lesion feature.

7. The CAD method of claim 1, wherein the additional information input area is further configured to display at least one additional information field having a greater influence on the diagnosis of the at least one lesion differently from at least one additional information field having a lesser influence on the diagnosis of the at least one lesion.

8. The CAD method of claim 1, wherein the additional information input area is further configured to receive at least one text-type additional information from the user.

9. The CAD method of claim 1, wherein the additional information input area is further configured to receive at least one audio-type additional information from the user.

10. A computer-aided (CAD) apparatus comprising:
    at least one processor configured to extract at least one lesion feature value from a captured lesion image comprising at least one lesion; and
    an interface configured to receive at least one additional information comprising information about the at least one lesion based on the captured lesion image,
    wherein the interface comprises a user interface comprising:
        a lesion image display area configured to display the captured lesion image, and
        an additional information input area configured to receive the at least one additional information, display at least one additional information field for selection by a user, and in response to one of the at least one additional information field being selected by the user, display at least one sub-field of the selected additional information field,
    wherein the at least one processor is further configured to diagnose the at least one lesion based on the extracted at least one lesion feature value and the received at least one additional information, and
    wherein the at least one additional information, that is based on the captured lesion image, affects a diagnosis of the at least one lesion.

11. The CAD apparatus of claim 10, further comprising a database configured to store a lesion diagnosis model,
    wherein the at least one processor is further configured to:
        compare the extracted at least one lesion feature value and the received at least one additional information with the lesion diagnosis model; and
        diagnose the at least one lesion based on a result of the comparing.

12. The CAD apparatus of claim 11, wherein the lesion diagnosis model is generated based on:
    at least one lesion feature value extracted from previously captured lesion images; and
    at least one additional information for the previously captured lesion images.

13. The CAD apparatus of claim 12, wherein the lesion diagnosis model comprises:
    at least one combination of the at least one lesion feature value extracted from the previously captured lesion images and the at least one additional information for the previously captured lesion images; and
    at least one diagnosis result corresponding to the at least one combination.

14. The CAD apparatus of claim 10, wherein the at least one additional information comprises at least one medical record and patient information that affect the diagnosis of the at least one lesion.

15. The CAD apparatus of claim 10, wherein the user interface is further configured to display, if at least one of the extracted at least one lesion feature value is less than a reference value, at least one additional information field for at least one corresponding lesion feature.

16. The CAD apparatus of claim 10, wherein the user interface is further configured to display at least one additional information field having a greater influence on the diagnosis of the at least one lesion differently from at least one additional information field having a lesser influence on the diagnosis of the at least one lesion.

17. The CAD apparatus of claim 10, wherein the additional information input area is further configured to receive at least one of text-type additional information and audio-type additional information from the user.

18. A method of generating a lesion diagnosis model, the method comprising:
    extracting at least one lesion feature value from each of captured lesion images;
    receiving, by a user interface, at least one additional information comprising information about the at least one lesion for each of the captured lesion images,
    wherein the user interface comprises:
        a lesion image display area configured to display at least one of the captured lesion images, and
        an additional information input area configured to receive the at least one additional information, display at least one additional information field for selection by a user, and in response to one of the at least one additional information field being selected by the user, display at least one sub-field of the selected additional information field;
    generating a lesion diagnosis model based on at least one combination of the at least one lesion feature value and the at least one additional information, and at least one diagnosis result corresponding to the at least one combination; and
    storing the generated lesion diagnosis model in a database, wherein the at least one additional information, that is based on the captured lesion image, affects a diagnosis of the at least one lesion.

19. The method of claim 18,
wherein each of the at least one combination comprises at least one lesion feature value and at least one additional information, and
wherein each of the at least one diagnosis result corresponds to at least one of the at least one combination.

20. The method of claim 18, wherein the at least one additional information comprises information about at least one lesion feature from which the at least one lesion feature value is extracted.

21. The method of claim 20, wherein the at least one additional information further comprises at least one medical record and patient information affecting the diagnosis of the at least one lesion from which the at least one lesion feature value is extracted.

22. The method of claim 18,
wherein the receiving comprises receiving the at least one additional information from the user, and
wherein the at least one diagnosis result corresponding to the at least one combination is determined by the user based on the captured lesion images.

* * * * *